United States Patent
Zhou

(10) Patent No.: US 6,861,135 B2
(45) Date of Patent: Mar. 1, 2005

(54) MICROWAVEABLE LATENT POLYMER COMPOSITES WITH ROUGH SURFACE TEXTURE

(75) Inventor: Peiguang Zhou, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 354 days.

(21) Appl. No.: 10/001,147

(22) Filed: Nov. 30, 2001

(65) Prior Publication Data

US 2003/0104190 A1 Jun. 5, 2003

(51) Int. Cl.[7] .............................................. B32B 3/26
(52) U.S. Cl. ..................... 428/323; 428/317.1; 428/332; 428/364; 428/400; 428/401; 428/402; 428/409
(58) Field of Search ............................ 264/230; 156/84, 156/85; 428/292, 317.1, 323, 332, 364, 400, 401, 402, 409

(56) References Cited

U.S. PATENT DOCUMENTS

| | | | | |
|---|---|---|---|---|
| 4,665,306 A | * | 5/1987 | Roland et al. | 219/388 |
| 5,127,977 A | * | 7/1992 | Eaton et al. | 156/244 |
| 5,250,587 A | * | 10/1993 | Peterson et al. | 523/137 |

FOREIGN PATENT DOCUMENTS

| | | | | |
|---|---|---|---|---|
| GB | 2 160 473 A | 12/1985 | ........... | B29C/55/00 |
| GB | 2 196 343 A | 4/1988 | ............ | C08K/3/00 |
| WO | WO 01/95753 A1 | 12/2001 | ............ | A41G/1/00 |
| WO | WO 02/47595 A1 | 6/2002 | ........... | A61F/13/15 |

* cited by examiner

Primary Examiner—Merrick Dixon
(74) Attorney, Agent, or Firm—Pauley Petersen & Erickson

(57) ABSTRACT

This invention relates to a latent polymer composite which contains a heat-sensitive polymer material and a microwave sensitizer. The latent polymer material is inelastic in the latent state but can be made elastic with the addition of heat. The microwave sensitizer is a solid material blended uniformly into the latent polymer composite. The sensitizer absorbs microwave radiation and heats the heat-sensitive polymer material. The polymer composite becomes elastic under microwave radiation or thermal energy. The latent polymer composite can bonded to a fibrous sheet to form a latent laminate material. When exposed to microwave radiation, the latent laminate material becomes an elastic laminate. The latent polymer composite of the laminate shrinks and returns to an elastic state creating an elastic laminate material. The polymer composite of this invention has a rough surface created by the sensitizer particles. The rough surface of the polymer filament or film provides stronger bonding to the fibrous sheets of the laminate.

42 Claims, 5 Drawing Sheets

MICROWAVEABLE LATENT POLYMER COMPOSITES WITH ROUGH SURFACE TEXTURE

FIELD OF THE INVENTION

This invention relates to a microwave sensitive latent polymer made of a blend of latent polymer material and a microwave sensitizer. The latent polymer composites of this invention use microwave energy to convert the latent polymer material to an elastic form. The latent polymer composites of this invention are useful in absorbent articles such as diapers.

BACKGROUND OF THE INVENTION

Elastic polymer materials are useful in absorbent articles. Elastic polymer strands or films can be used, for instance, in waist and leg regions of a wearable absorbent article such as a diaper. The resulting elastic waist and leg regions provide a secure fit to the user. This helps stop leaking as well as makes the diaper more comfortable.

Absorbent articles contain many materials and the manufacturing process can be complex and expensive. Manufacturing methods that simplify production and reduce cost are desired. One method of making elastic laminates involves stretching an elastic material, such as a strand or film, and bonding the stretched material to a fabric sheet to create an elastic laminate. Some elastic polymers, when stretched, will maintain the stretched, or latent, state until heat is added to restore the elasticity. Heating latent polymers to restore elasticity is useful in producing absorbent articles but this process can also require numerous production steps and can become expensive.

Microwave energy has primarily been used for food processing. Microwave sensitive materials have been used to increase microwave heating rate and uniformity. Most microwave sensitive materials are inorganic chemicals and are typically coated onto a substrate to form a microwave interactive layer. Often times there is little control over the amount of heat produced by these materials, which can result in inadequate heating or overheating and burning.

There is a need in the absorbent article industry for new ways to heat latent polymer materials quickly and efficiently.

SUMMARY OF THE INVENTION

This invention relates to a latent polymer composite which contains a heat-sensitive polymer material and a microwave sensitizer. The latent polymer material is inelastic in the latent state but can be converted to an elastic state with the addition of heat. The microwave sensitizer is a solid material blended (preferably uniformly) into the latent polymer material. The sensitizer absorbs microwave radiation and heats the heat-sensitive polymer material. The polymer composite becomes elastic due to the heat from the sensitizer.

In one embodiment of this invention the latent polymer composite is bonded to a fibrous sheet to form a laminate material. When exposed to microwave radiation, the laminate material becomes elastic. The latent polymer composite of the laminate shrinks and converts to an elastic state creating an elastic laminate material. The polymer composite of this invention has a rough surface produced by the sensitizer particles. The rough surface provides more surface area for the bonding material to adhere to resulting in stronger bonding to the fibrous sheets of the laminate. The stronger bonding in the laminate increases the creep resistance of the laminate material. The resulting laminate is a strong, elastic material useful in absorbent articles.

DEFINITIONS

Figure 1:
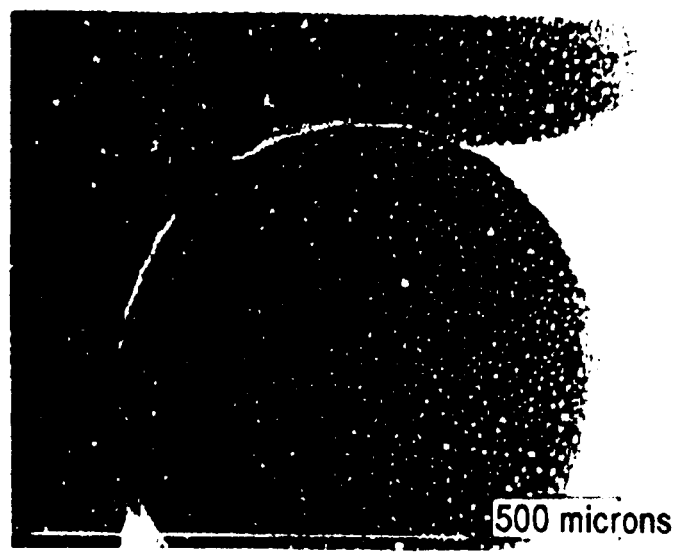
FIG. 1 is a photograph of a cross-section of a polymer composite strand according to one embodiment of this invention.

Within the context of this specification, each term or phrase below will include the following meaning or meanings.

"Absorbent article" includes diapers, training pants, swim wear, absorbent underpants, adult incontinence products, feminine hygiene products, absorbent wipes, medical garments, and the like. The term "medical garment" includes medical (i.e., protective and/or surgical) gowns, caps, gloves, drapes, face masks, blood pressure cuffs, bandages, veterinary products, mortuary products, and the like.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Cross direction" refers to the width of a fabric in a direction generally perpendicular to the direction in which it is produced, as opposed to "machine direction" which refers to the length of a fabric in the direction in which it is produced.

"Elastic" means that property of a material or composite by virtue of which it tends to stretch when exposed to a stretching force, and to recover most or all of the way to its original size and shape after removal of the stretching force. An elastic material should be able to stretch in at least one direction by at least 50% of its initial (unstretched) length without rupturing, and should immediately recover more than 50% of the way to its initial length when the stretching force is removed.

"Fibrous sheets" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Layer" when used in the singular can have the dual meaning of a single element or a plurality of elements.

"Latent" refers to a non-elastic state of a polymer composite. A latent polymer composite can be made by stretching an elastic polymer composite to a certain stretched ratio at which the polymer composite no longer has elastic characteristics. The stretched polymer composite is in a latent state when there is substantially less elastic recovery towards the unstreched length or no elastic recovery at all. The latent polymer composite is maintained in the latent state by high intermolecular forces, such as hydrogen bonding or ionic association between polymer molecules, and/or crystallization of polymer molecules. The polymer composite can be made latent at about room temperature (~23° C.) or below, or any other temperature when the intermolecular forces and/or crystals can form. Because latent polymer composites are in a stretched, non-equilibrium state, they are generally temperature sensitive. Latent polymer composites can regain elastic characteristics when the intermolecular forces maintaining the stretched polymer are overcome by applying thermal energy, such as melting the crystals holding the polymer composite in the latent state. The latent polymer composite has little or no recovery towards the original unstretched length until the crystals are melted by the addition of heat.

"Leg elastic" includes elastic bands, strands, ribbons, filaments, filament bunches and the like, which are adjacent to a garment opening that receives a wearer's leg.

"Machine direction" refers to the length of a fabric in the direction in which it is produced, as opposed to "cross direction" which refers to the width of a fabric in a direction generally perpendicular to the machine direction.

"Microwave activation" refers to the use of microwave energy to return a latent polymer to its elastic state. Microwave activation generates heat by microwave radiation which overcomes the hydrogen bonding, ionic association between polymer molecules, and/or crystallization of polymer molecules that holds the polymer in the latent state.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven sheets" refer to fibrous materials and webs of fibrous material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Sensitizer material" refers to any material with a high microwave absorbency that generates thermal energy as a result of contact with microwave radiation.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Thermoplastic" describes a polymer material that softens and flows when exposed to heat and which substantially returns to a nonsoftened condition when cooled to room temperature.

"Waist elastic" includes elastic bands, strands, ribbons, filaments, filament bunches and the like, which are adjacent to a garment opening that receives a wearer's waist.

These terms may be defined with additional language in the remaining portions of the specification.

DETAILED DESCRIPTION OF THE PRESENTLY PREFERRED EMBODIMENTS

Polymer composites of this invention are useful in personal care absorbent articles such as diapers. Elastic polymer composites, such as polymer strands, filaments, or films, are especially useful in stretchable areas of absorbent articles and are generally used to fit the absorbent article to the user. In one embodiment of this invention elastic polymers composites are used in the waist and/or leg regions of a diaper. The polymer composites when in the elastic state, provide a snug fit to the user to diminish leaking of bodily wastes held in the diaper. Using the latent polymer composites of this invention to manufacture absorbent articles and then activating the latent polymer material to become elastic simplifies manufacturing and reduces cost.

Latent polymer composites of this invention can start out or be physically changed into a latent state, which is maintainable at a lower temperature such as room temperature, and can be converted to an elastic state by an increase in temperature. "Latent" refers to a non-elastic state of a polymer composite. A latent polymer composite can be made by stretching an elastic polymer composite to a certain stretched ratio at which the polymer composite no longer has elastic characteristics. The stretched polymer composite is in a latent state when there is substantially less elastic recovery towards the unstreched length or no elastic recovery at all. The latent polymer composite is maintained in the latent state by high intermolecular forces, such as hydrogen bonding or ionic association between polymer molecules, and/or crystallization of polymer molecules. The polymer composite can be made latent at about room temperature (~23° C.) or below, or any other temperature when the intermolecular forces and/or crystals can form. Because latent polymer composites are in a stretched, non-equilibrium state, they are generally temperature sensitive. Latent polymer composites can regain elastic characteristics when the intermolecular forces maintaining the stretched polymer are overcome by applying thermal energy, such as melting the crystals holding the polymer composite in the latent state. The latent polymer composite has little or no recovery towards the original unstretched length until the crystals are melted by the addition of heat. The returning of a latent polymer composites to a state of equilibrium, in which the polymer is elastic, is referred to as "activation" of the latent polymer composites. Examples of polymers that can be used to form composites that can be made latent include, without limitation, polyethers, polyamines, polyesters, and polyurethanes.

Figure 2:
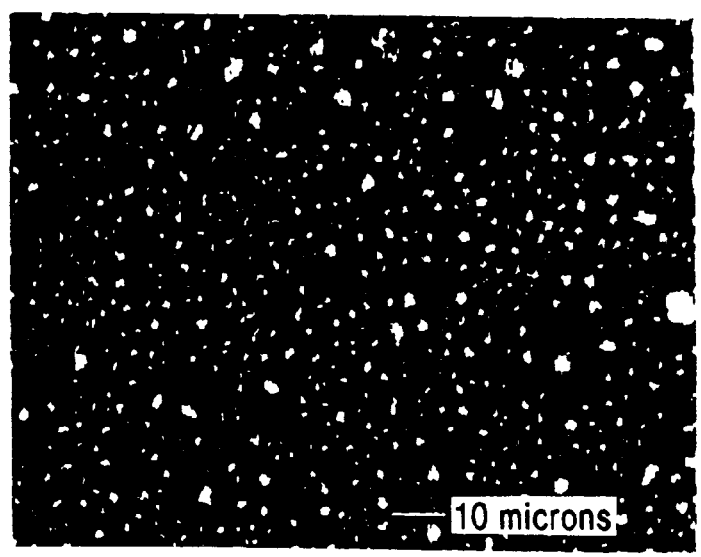
FIG. 2 is a photograph of a cross-section of a polymer composite strand according to one embodiment of this invention.

Latent polymer composites of this invention are blended (preferably melt blended) with a microwave sensitizer material before they are converted to the latent state. FIGS. 1 and 2 are electron microscope images showing the lighter sensitizer particles blended within the darker polymer material. Sensitizer materials react to microwave energy and release heat. The blended polymer composite can be stretched to form a latent polymer composite. When microwave energy is applied to the latent polymer composite the sensitizer material converts the microwave energy to heat. The heat produced by the sensitizer material activates the latent polymer composite and returns the latent polymer composite to an elastic state. Alternatively, the latent polymer composite with blended sensitizer material can be activated using thermal energy, such as heat, instead of microwave energy, in the same fashion as a latent polymer without the sensitizer is activated. Because of the sensitizer material, activation of the latent polymer composite with blended sensitizer material by thermal energy is also more efficient than activation of the latent polymer composite without blended sensitizer material.

Polymer materials useful as the latent polymer material of this invention include thermoplastic elastomers. In one embodiment of this invention the polymer material is a polyether-b-block amide. Polyether-b-block amides useful in this invention are manufactured by Elf ATOCHEM, King of Prussia, Pa., under the general name PEBAX®. The structure of PEBAX® polymers consist of multiple rigid polyamide blocks and flexible polyether blocks. A generalized structure is shown by the formula:

Through the proper combination of polyamide and polyether blocks, a wide range of polymers with varying performance characteristics are possible. PEBAX® 2533 is one example of a preferred polymer material because of its good elasticity, low hysteresis, latency characteristics, and breathability.

Another polymer material useful in this invention is manufactured by Exxon, Houston, Tex., under the name Exxon 601. Exxon 601 is a proprietary polymer (U.S. Pat. Nos. 4,714,735 and 5,182,069) comprising from about 20 to about 30% by weight olefinic elastomer, from about 60 to 75% by weight ethylene copolymer, from about 4 to 10% by weight processing oil, and less than about 5% by weight other additives. Other useful polymer materials include, without limitation, ethylene-vinylacetate block or random copolymers, polyethylene-polyethylene oxide block copolymers, polypropylene oxide-polyethylene oxide block copolymers, polyesters, polyurethanes, polyacrylates, polyethers, and combinations thereof.

Using latent polymer materials in manufacturing absorbent articles instead of elastic polymers reduces manufacturing steps and cost. Microwave activatable latent polymer materials provide additional manufacturing benefits. The polymer material alone, without a sensitizer material, has a low dielectric loss factor and therefore is not easily activated by microwave energy. By adding a sensitizer material which is interactive with microwave radiation to the polymer material the latent polymer composites can be quickly activated by microwave energy due to increased dielectric loss factor.

Most known sensitizer materials are made from inorganic chemicals such as aluminum, copper, zinc, oxides of aluminum, copper, and zinc, and various ferrites including without limitation barium ferrite, magnesium ferrite, and carbon black. Many known sensitizer materials generally offer little control of how much heat is generated and how quickly. Sensitizer materials are generally coated onto a surface of an object to be heated and the heat generated slowly permeates the object from the surface inward. Because the sensitizers heat the surface first, the heating is not typically uniform throughout the object. Using sensitizer material in this regard is not unlike the heating done by hot air, where the hot air heats a surface of an object first and then the energy gradually permeates the object while raising its overall temperature. It has been discovered that some sensitizers can be uniformly blended in solid form with polymer materials to create a latent polymer/sensitizer composite which, in the presence of microwave energy, will generate proper, uniform amounts of heat to activate the latent polymer material. The heat generation by the blended sensitizers throughout the composite increases the rate of composite heating and lowers the overall energy necessary to heat the composite.

Sensitizer materials useful in this invention include calcium chloride and carbon black powder. Other sensitizer materials useful in this invention include, without limitation, metal particles, metal oxides such as aluminum, copper, zinc, and their oxides, various ferrite containing materials such as barium ferrite and magnesium ferrite, magnesium acetate, and combinations thereof. Polymer composites of this invention contain between about 1% and 20% by weight sensitizer material, more suitably between about 1% and 15% by weight sensitizer material, and desirably between about 2% and 8% by weight sensitizer material.

In one embodiment of this invention a polymer material is blended with a sensitizer material and the blend is extruded into polymer filaments. In one embodiment the sensitizer material is blended into melted polymer material before forming a filament or film. In one embodiment the polymer-sensitizer blend is mixed by twine extruder during a melting process and formed into pellets. The pellets of the compound are extruded by a twine extruder into filaments. The filaments are then stretched by vertical filament laminate process to create latent polymer filaments at or below room temperature. The vertical filament laminate process includes stretching the extruded filaments using one or more series of stretch rolls. Each series of stretch rolls may include one or more individual stretch rolls, and desirably at least two stretch rolls. Where more than one series of stretch rolls are used, a latter series of stretch rolls rotates at a speed greater than the speed of a former series of stretch rolls, thereby stretching the nonwoven fabric.

In one embodiment, each successive roll rotates at a speed greater than the speed of the previous roll. For example, a first stretch roll may rotate at speed "x"; a second stretch roll rotates at a speed greater than "x", for example about "1.1x"; a third stretch roll rotates at a still greater speed, for example about "1.15x"; and a forth stretch roll rotates at a still greater speed, for example about "1.25x" to about "2x." As a result, filaments can be stretched by about 100% to about 800% of an initial length, or by about 200% to about 700% of an initial length. The stretching process can be done using various rolls at various speeds or using other filament stretching processes known in the art.

Polymer composites of this invention are elastic at room temperature (~23° C.) and must be stretched to a certain length to place the polymer strands in the non-elastic latent state. Elastic composites of this invention are generally stretched at least about 100–800% of the initial non-stretched length to create a latent polymer composite. The latent polymer strands are then used as desired in manufacturing an absorbent article. The latent polymer strands can be activated by exposure to microwave energy at any time as desired depending on the manufacturing process and the type of absorbent article made. Polymer strands of this invention may have a thickness of between about 0.1 mm and 2.0 mm when in the latent state.

In one embodiment of this invention the polymer composite compound is formed into a latent polymer film. The latent polymer film can be made by any method known in the art such as cast or blown film extrusion. Polymer composite films of this invention are formed from molten polymer composite, cooled, and then stretched by various techniques at about room temperature (~23° C.) to obtain a latent polymer film. Latent polymer strands and films can be used in the manufacture of absorbent articles and returned to an elastic state by either microwave energy, thermal energy, or combinations thereof. The thickness of the elastic polymer films or filaments can vary depending upon the final use of the films or filaments. Production of films according to this invention is done by using a extruder with a film die instead of a filament die.

In one embodiment of this invention at least one latent polymer filament is placed between fibrous sheets, such as thermoplastic nonwoven sheets including without limitation spunbond or meltblown nonwoven sheets, and bonded to the nonwoven sheets with or without hot melt adhesive, provided the hot melt adhesive is not too hot (a temperature below the melting point of the polymer is generally useable) so the adhesive does not activate the latent polymer filament, to form latent polymer laminates. The laminates can be activated either by microwave energy or thermal energy to return the latent polymer material to an elastic state. The resulting elastic laminates are useful in absorbent articles. In one embodiment of this invention the elastic laminates are used in at least one of a waist region and leg regions of a diaper. Latent polymer films can also be used to create laminates with nonwoven sheets.

Microwave energy is an electromagnetic energy which has wavelengths from 1.0 centimeters to 1.0 meters corresponding to frequencies in the range of $3 \times 10^8$ to $3 \times 10^{10}$ hertz. Frequencies suitable for use in this invention for activating latent polymer composites are either 2415 megahertz or 915 megahertz. Generally, microwave energy is absorbed by molecules through the polarization or dipole reorientation of the functional groups, and/or by ionic movements, which is translated into thermal energy. As a result, materials can be heated using microwave irradiation at the molecular level. The heat is generated within each molecule and thereby a uniform heating pattern can be created in the material. In this manner, the material can be heated very efficiently as compared to conventional heating.

Microwave heating of a material is dependent on the dielectric properties of the material. The dielectric properties of a material can be described by two parameters, the dielectric constant and the dielectric loss factor. If the dielectric loss factor is too low, the material will not absorb microwave radiation, regardless of microwave power. The higher the dielectric loss factor of the material, the higher the heating rate can be. Generally, it is desired that a sensitizer material of this invention will permit the microwave power to be greater than about 800 watts, more desirably to be greater than about 3.0 kilowatts, and most desirably greater than 6.0 kilowatts. The greater the dielectric loss factor of the sensitizer material and the greater amount of sensitizer material, the greater the amount of heat released and the greater the rate and degree of shrinking capacity. Polymer composites of this invention suitably contain between about 10% and 20% by weight sensitizer material, more suitably between about 10% and 15% by weight sensitizer material, and desirably between about 2% and 8% by weight sensitizer material.

Desirably the sensitizer material is activated using a high speed microwave activation process. The process desirably uses a microwave oven set at a power of 900 watts and a frequency of about 2450 megahertz. Conventional microwave ovens can be used to activate the sensitizer material.

Figure 3:
FIG. 3 is a photograph of a polymer composite strand according to one embodiment of this invention.
Figure 4:
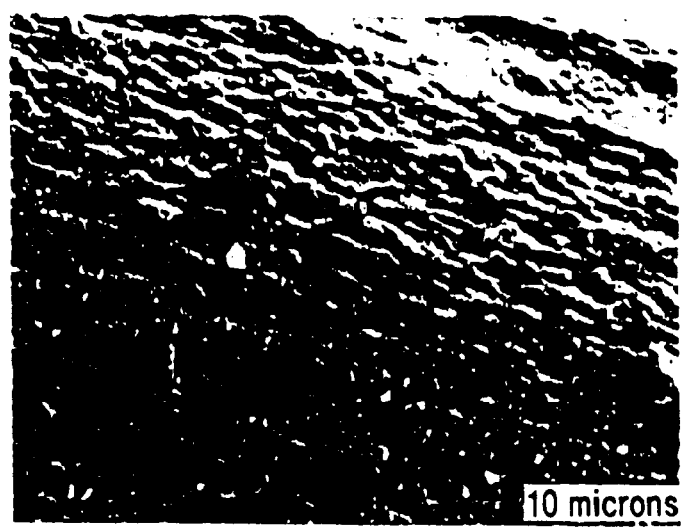
FIG. 4 is a photograph of a polymer composite strand according to one embodiment of this invention.

Blending solid particles of a microwave material into a polymer material to create a polymer filament or film has an additional benefit in that the resulting strand or film has a rough surface texture. As shown in FIG. 3, a PEBAX® polymer filament has a smooth surface texture both in a latent state and a elastic state. As shown in FIG. 4, a PEBAX® polymer filament having a microwave sensitizer material according to this invention has a rough surface texture. In one embodiment of this invention the rough surface texture of the latent polymer filament having a sensitizer material provides a stronger bonding to nonwoven sheets. The rough surface of the latent polymer filament allows better bonding of an adhesive material and results in a stronger polymer strand/nonwoven sheet laminate.

Latent polymer composites of this invention have sensitizer materials distributed fairly uniformly throughout the latent polymer composite. In one embodiment of this invention the amount of sensitizer material in the latent polymer composite is suitably at least about 0.1 grams sensitizer material/gram polymer material. Suitably the amount of sensitizer material in the latent polymer composite is about 10% to 20% by weight. The uniform distribution provides even heating of the latent polymer composite when exposed to microwave energy and a uniform rough surface texture provides better bonding with adhesive materials. Uniform heating can also be influenced by sensitizer particle size. Sensitizer particle diameter can vary and is suitably in a range from sub-micron to about 10 microns. In one embodiment of this invention the suitable average diameter of the sensitizer particles is about 0 and 25 microns, more suitably between about 5 and 10 microns, and desirably between about 1.5 and 2.5 microns.

In one embodiment of this invention, an activated laminate has improved elastic composite creep resistance. "Activated laminate" refers to a laminate material having at least one latent polymer composite with sensitizer material as one layer of the laminate, and wherein the latent polymer composite has been activated by thermal or microwave energy to return to an elastic state. When the polymer composites of the laminate material are latent polymer composites then the laminate material is referred to as a latent laminate material.

It is fairly difficult to securely bond a pure PEBAX® latent strand in a laminate by conventional hot melt adhesive. Upon activation the PEBAX® strand loses adhesion due to structure and morphology changes. Due to the lost adhesion, the activated polymer strands move within the laminate. This movement is referred to as "creeping." Activated PEBAX® strands, as an example, typically exhibit more than 50% creep when used in a nonwoven laminate. It has been discovered that a latent polymer composite having a blended sensitizer material not only has a faster microwave and hot air activation speed, but also exhibits less creep than a latent polymer composite without a sensitizer material. Less creep of the polymer composites of this invention is due in part to the bonding improvement of the rough surface texture and the surface tension change.

Figure 5:
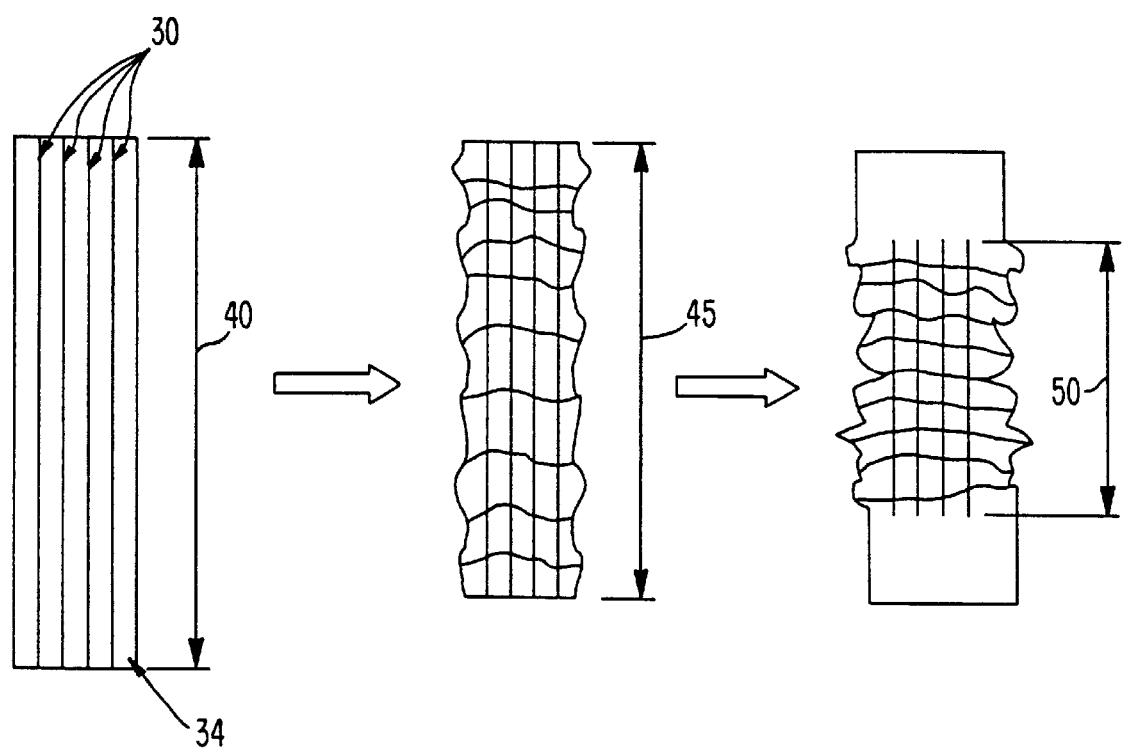
FIG. 5 shows a schematic diagram of creep testing.

A sample creeping test is shown in FIG. 5. Elastic strands 30 are spaced apart approximately 2.5 mm in the cross-direction, each elongated approximately 150% to 300% and adhesively attached and sandwiched between two 4-inch wide continuous polypropylene spunbonded layers 34 to form a laminate. The laminate is fully extended by hanging a weight (about 500 grams or higher) at one end of the laminate, and a first machine-direction length 40 is then marked. The laminate is then released, such that the first machine-direction length 40 is snapped back to a second machine-direction length 45, whereupon the second machine-direction length 45 is marked. The laminate is then stapled to a piece of cardboard at the second machine-direction length 45. The marked length of the laminate is then cut to release tension in the elastic strands 30, and the snapback length 50 of the strands is measured.

Initial creep percentage is calculated by first determining the difference between the second machine-direction length 45 (second length) and the snapback length 50, then dividing the difference by the second machine-direction length 45 and multiplying the quotient by 100, as shown in the following equation:

Initial Creep %=(second length−snapback length)/second length×100

The sample is then placed in an oven at 100° Fahrenheit, or other suitable temperature, for 90 minutes to measure aging creep. Aging creep percentage is then calculated by determining the difference between the second machine-direction length 45 and that snapback length 50, then dividing the difference by the second machine-direction length 45 and multiplying the quotient by 100, as shown in the following equation:

Aging Creep %=(second length−aged snapback length)/second length×100

Snapback length readings used in the calculations can be an average of the snapback length of multiple samples.

Activated laminates having polymer strands having blended sensitizer materials according to this invention exhibit less creeping than activated laminates having polymer strands without sensitizer materials. Activated laminates having polymer strands having blended sensitizer materials according to this invention generally exhibit a creeping percentage less than about 50%, more suitably less than about 30%, more suitably less than 20%, and most suitably less than 10%. Laminates made with PEBAX® not having blended sensitizer material typically creep about 50% to 70% and laminates made with PEBAX® having blended sensitizer material according to this invention creep at about less than 30% and typically about 10% to 15%.

To further illustrate the invention and demonstrate some of the advantages the following examples were prepared. The examples are not intended to limit the invention and it should be understood that variations of these examples are available which would also demonstrate the invention.

EXAMPLES

A blend of PEBAX® 2533 (92% by weight) and calcium chloride, $CaCl_2 \cdot 2H_2O$, (8.0% by weight) was premixing manually and then compounded by a Brabender twine extruder available from C.W. Brabender Instruments, Inc., New Jersey, in the temperature range of about 200–235° C. Thermal analysis of PEBAX® 2533 (PEBAX) and the blends (PEBAX/$CaCl_2$ blend) was performed by differential scanning calorimetry (DSC) and thermogravimetric analysis (TGA).

Thermogravimetric analysis measurements were carried out using TA Instruments 951 Thermal Gravimetric Analyzer connected to a 2100 Controller. The samples were heated from room temperature to 450° C. with a heating rate of 10° C./min under a dynamic atmosphere of air with air flow of approximately 80 ml/min. A separate control sample PEBAX was analyzed at 10° C./min under a dynamic atmosphere of nitrogen ($N_2$) with a flow of 80 ml/min. The flow rate was monitored with a flow cell having a scale of 0 to 100 ml/min.

The thermal and oxidation stability of PEBAX and the PEBAX/$CaCl_2$ blend were evaluated by TGA in nitrogen and air separately. Thermograms for PEBAX showed oxidation degradation in air occurring at about 195° C. and thermal degradation in a nitrogen atmosphere at about 350° C. Thermograms for the PEBAX/$CaCl_2$ blend showed degradation in air at about 350° C., representing an increased oxidative stability in air over pure PEBAX. The enhanced thermal oxidative stability of PEBAX/$CaCl_2$ blend may be due to physical crosslinking in which the $Ca^{+2}$ associated with the carbonyl or ether groups of PEBAX and limited oxygen penetration into the blend.

Differential Scanning Calorimetry analysis was performed using a TA Instruments 2920 Differential Scanning Calorimeter (DSC) with both a single sample cell and a dual sample cell. The samples tested included PEBAX pellets, PEBAX strands stretched to 400%, 600%, and 800%, PEBAX/$CaCl_2$ blend pellets, and PEBAX/$CaCl_2$ blend strands stretched to 700%. The samples were heated from −100° C. to 250° C. at a rate of 10° C./min under a dynamic atmosphere (50 ml/min) of nitrogen for the PEBAX samples and air for the PEBAX/$CaCl_2$ blend samples.

Figure 6:
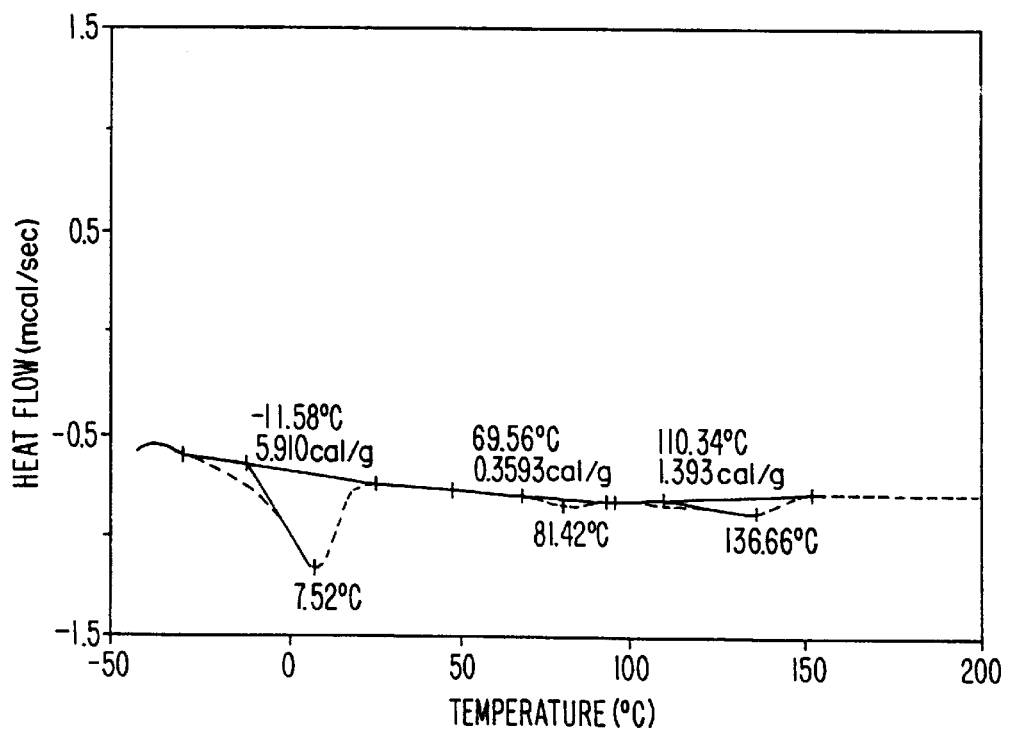
FIG. 6 is a DSC spectra of a polymer without sensitizer material.
Figure 7:
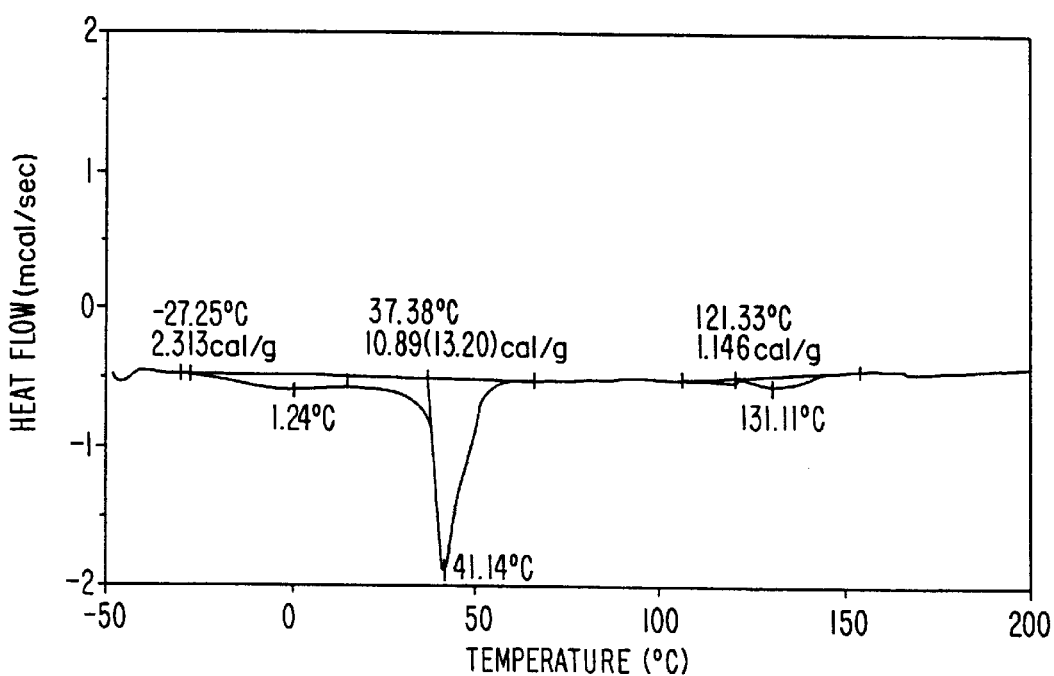
FIG. 7 is a DSC spectra of a polymer without sensitizer material stretched to 600%.

FIG. 6 shows a DSC spectrum for PEBAX pellets. FIG. 7 shows a DSC spectrum for PEBAX strands stretched to 600%. The DSC spectra of PEBAX strands stretched to 400%, 600%, and 800% clearly indicated that latency of a PEBAX strand is due to stress inducing crystallization. The DSC spectra of the stretched PEBAX strands showed the crystallization peak in the range of about 40° C. to 45° C. for each stretch ratio. Taking into account instrument error, one can see the melting point of the PEBAX is not substantially related to the stretch ratio. Furthermore, the DSC spectra showed the enthalpy of melting ($\Delta H$ J/g) was increased as the stretching percent increased, which indicated more crystallization of the polymer chains occurred at a higher stretch. Table 1 summarizes the stress-induced crystallization and melting points of PEBAX strands under different stretching ratios.

TABLE 1

| Stretch (%) | Stress-induced crystallization ($\Delta H$ J/g) | Melting Point (° C.) |
| --- | --- | --- |
| 400 | 46.1 | 43.4 |
| 600 | 54.4 | 41.2 |
| 800 | 86.1 | 45.8 |

Figure 8:
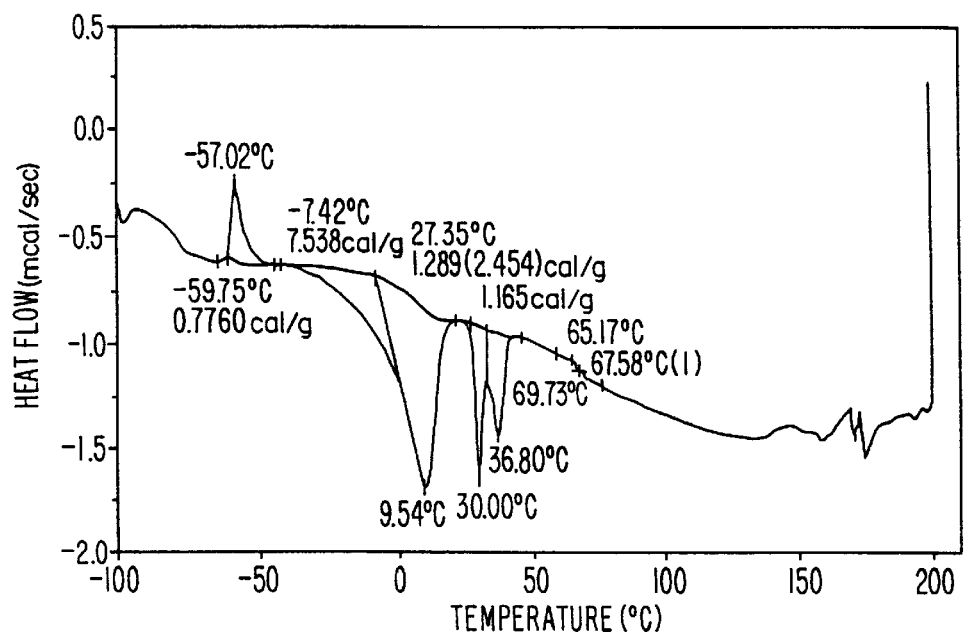
FIG. 8 is a DSC spectra of a composite according to one embodiment of this invention.

PEBAX/$CaCl_2$ blend pellets and strands stretched to about 700% original size were also tested by DSC. FIG. 8 shows a DSC spectrum of PEBAX/$CaCl_2$ blend pellets. FIG.

Figure 9:
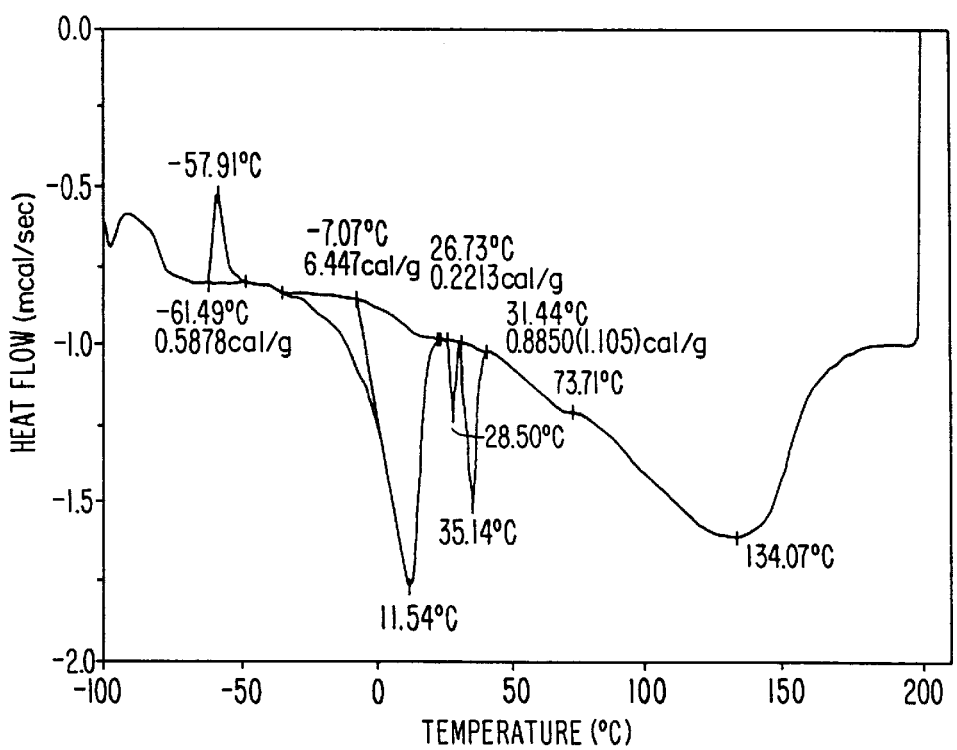
FIG. 9 is a DSC spectra of a composite according to one embodiment of this invention.

9 shows a DSC spectra for PEBAX/CaCl$_2$ blend strands stretched to 700%. As shown in FIG. 8 the melting point of the PEBAX/CaCl$_2$ blend pellets was at about 30° C. (the peak at about 9.54° C. is the melting point of the polyether block of the PEBAX) as compared to the melting point of the PEBAX pellets of about 7.52° C. As shown in FIG. 9 the melting point of the PEBAX/CaCl$_2$ blend is at about 28.50° C. as compared to about 41.2 the PEBAX strand at 600%. In addition to having lower melting points the PEBAX/CaCl blend samples exhibited a lower enthalpy of melting. The lower melting point and lower enthalpy of melting of the PEBAX/CaCl$_2$ blend than the PEBAX results in less energy required for activation.

The morphology of strands and pellets of the PEBAX and PEBAX/CaCl$_2$ blend was studied by scanning electron microscopy (SEM). Each sample was sectioned to provide a smooth, flat surface for electron imaging. Visualization of the calcium chloride particles within the PEBAX matrix was optimized using atomic number contrast imaging in the SEM. Backscatter electron images were collected from the planed block faces using a Galileo Electronics microchannel plate electron detector (MOP) in a JEOL 6400 scanning electron microscope at 1.4 kV for direct imaging of the sample (without coating covered). Bright phase particle imaging and X-ray analysis confirmed the uniform displacement of the calcium chloride particles in the PEBAX. The average particle size was measured by a PGT MIX microanalyzer system.

The PEBAX and PEBAX/CaCl$_2$ blend were used to make laminates for testing differences in activation rates by microwave and hot air and also for creep testing. The PEBAX laminate was used as a control to see the benefits of the PEBAX/CaCl$_2$ blend. Laminates were made by attaching one of PEBAX or PEBAX/CaCl$_2$ blend to 0.4 osy polypropylene spunbond fabric by hot melt adhesives H2800 and H2096, available from AtoFindley Adhesives, Inc., Milwaukee, Wis. PEBAX and PEBAX/CaCl$_2$ blend strands were made by a vertical filament lamination extrusion system. The filaments were extruded and stretched 700% between the nips of two rollers and had a final basis weight of 50–70 gsm. The stretched latent filaments were then sandwiched and glued between two 0.4 osy spunbond layers with 12 gsm hot melt adhesive H-2096. The laminate size was 55×200 mm with about 11–12 strands in each laminate. The resulting laminate was maintained in a flat, non-elastic state with minimal relaxation before activation.

Microwave energy and conventional hot air were each used to activate both the PEBAX and PEBAX/CaCl$_2$ blend laminates. A conventional microwave-cooking oven (Sharp Mode Carousel) was used as a screen tool for primary evaluation of microwave sensitivity of the laminates. The output power of the microwave oven was 900 W with a frequency of 2450 MHZ and the microwave had a Teflon support plate to minimize microwave energy absorption by the glass plate. Hot air activation of the laminates was done using a forced-air oven at both 60° C. and 75° C. at time periods to get maximum shrinkage as a comparison to the microwave activation process.

Activation of the laminate samples were carried out in both the conventional oven and a microwave oven separately. The results of the percent shrinkage of the laminates at various times during activation are summarized in Table 2. Percent shrinkage of the laminates at a given time is equal to the original length minus the length after activation divided by the original length. The greater the percent shrinkage the more activation of the laminates has occurred. A higher shrinkage of the laminate by one activation method than another at the same activation time indicates higher efficiency of that activation method. The results in Table 2 indicate that both microwave and hot air activation of the PEBAX/CaCl$_2$ blend are more efficient than those of pure PEBAX strands stretched at the same ratio.

TABLE 2

|  | Time (seconds) | | | | | |
| --- | --- | --- | --- | --- | --- | --- |
|  | 3 | 4 | 5 | 10 | 15 | 30 |
| Microwave PEBAX | 0 | 0 | 0 | 23% | 30% | 47% |
| Microwave PEBAX Blend | ~35% | ~45% | ~50% | ~50% | | |
| 75° C. Hot Air PEBAX | | | 42% | 54%* | 56% | 58% |
| 75° C. Hot Air PEBAX Blend | | | 60% | 62%* | 62% | 62% |
| 60° C. Hot Air PEBAX | | | | 45% | 50% | |
| 60° C. Hot Air PEBAX Blend | | | | 56% | 60% | |

(*these results were recorded at 8 seconds)

The PEBAX and PEBAX/CaCl$_2$ blend laminates were then tested according to a creeping test. The laminates were in the nonelastic latent state originally, then activated either by microwave or hot air to gain maximum elasticity (activation). The activated laminates had about a 100 mm length. The activated laminates were fully extended and released back 25% (to a length of about 130–135 mm), stapled to a piece of cardboard, marked at 100 mm, the original length, and cut at the marked length. Initial creep percent was taken by measuring the snapback length from the original 100 mm mark after cutting, and divided by the original length 100 mm. The sample was then placed in an oven at 100° F. for 90 minutes to measure aged creeping. Aging creep percent was then calculated by measuring the snapback length of the strands and dividing by 100 mm.

Not only did the PEBAX/CaCl$_2$ blend exhibit a much faster microwave and hot air activation rate, the PEBAX/CaCl$_2$ blend also showed greater creeping resistance than the pure PEBAX strands. The pure PEBAX strands had an initial creep of about 50–60% and an aged creep of about 55%–60%. The PEBAX/CaCl$_2$ blend had an initial creep of 15–25% and an aged creep of about 25–30%. The greater creep resistance of the PEBAX/CaCl$_2$ blend is most likely due to the rough surface and surface tension change created by the calcium chloride particles, resulting in better bonding to the substrate.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

I claim:

1. A laminate material, comprising:
    at least one polymer composite comprising a heat-sensitive latent polymer material and a microwave sensitizer material blended with the heat-sensitive polymer material; and
    a nonwoven sheet bonded to the polymer composite.

2. The laminate of claim 1, wherein the polymer composite further comprises a rough surface texture.

3. The laminate of claim 1, wherein the nonwoven sheet comprises a material selected from the group consisting of a spunbond sheet, a meltblown sheet, and combinations thereof.

4. The laminate of claim 1, wherein the latent polymer material comprises a stretched elastic polymer material.

5. The polymer composite of claim 1, wherein the polymer composite comprises a material selected from the group consisting of a polymer filament, a polymer film, and combinations thereof.

6. The laminate of claim 1, wherein the heat-sensitive polymer material comprises one selected form the group consisting of polyether-block amides, ethylene-vinylacetate block or random copolymers, polyethylene-polyethylene oxide block copolymers, polypropylene oxide-polyethylene oxide block copolymers, polyesters, polyurethanes, polyacrylates, polyethers, and combinations thereof.

7. The laminate of claim 1, wherein the sensitizer material comprises a material selected from the group consisting of carbon black powder, calcium chloride, aluminum oxide, copper oxide, zinc oxide, barium ferrite, magnesium ferrite, magnesium acetate, and combinations thereof.

8. The laminate of claim 1, wherein the laminate comprises a creeping percentage less than about 50%.

9. The laminate of claim 8, wherein the laminate comprises a creeping percentage less than about 30%.

10. The laminate of claim 9, wherein the laminate comprises a creeping percentage less than about 20%.

11. The laminate material of claim 1, wherein the sensitizer material comprises sensitizer particles including an average diameter of less than about 25 microns.

12. The laminate material of claim 11, wherein the sensitizer particles include an average diameter of about 1.5 to about 2.5 microns.

13. The laminate material of claim 1, wherein the polymer composite includes about 1% to about 20% by weight of the sensitizer material.

14. The laminate material of claim 13, wherein the polymer composite includes about 2% to about 8% by weight of the sensitizer material.

15. A laminate, comprising:
an elastic polymer composite including an elastic polymer material and a microwave sensitizer material blended with the elastic polymer material; and
a fibrous sheet bonded to the elastic polymer composite.

16. The laminate of claim 15, wherein the elastic polymer composite is stretched to form a latent polymer composite and the latent polymer composite is bonded to the fibrous sheet and exposed to at least one of microwave energy and thermal energy to form an elastic laminate.

17. The laminate of claim 15, wherein the elastic polymer composite comprises one of a filament, a film, and combinations thereof.

18. The laminate of claim 15, wherein the elastic polymer material is selected from a group consisting of polyether-block amides, ethylene-vinylacetate block or random copolymers, polyethylene-polyethylene oxide block copolymers, polypropylene oxide-polyethylene oxide block copolymers, polyesters, polyurethanes, polyacrylates, polyethers, and combinations thereof.

19. The laminate of claim 15, wherein the sensitizer material is selected from a group consisting of carbon black powder, calcium chloride, aluminum oxide, copper oxide, zinc oxide, barium ferrite, magnesium ferrite, magnesium acetate, and combinations thereof.

20. The laminate of claim 15, wherein the sensitizer material comprises sensitizer particles including an average diameter about 25 microns or less.

21. The laminate of claim 20, wherein the sensitizer particles include an average diameter of about 5 to about 10 microns.

22. The laminate of claim 21, wherein the sensitizer particles include an average diameter of about 1.5 to about 2.5 microns.

23. The laminate of claim 15, wherein the sensitizer material is substantially uniformly blended with the elastic polymer material.

24. The laminate of claim 15, wherein the elastic polymer material includes about 1% to about 20% by weight of the sensitizer material.

25. The laminate of claim 24, wherein the elastic polymer material includes about 1% to about 15% by weight of the sensitizer material.

26. The laminate of claim 24, wherein the elastic polymer material includes about 2% to about 8% by weight of the sensitizer material.

27. The laminate of claim 15, wherein the elastic polymer composite includes a rough surface texture.

28. The laminate of claim 15, wherein the fibrous sheet is bonded to the elastic polymer composite by hot melt adhesive.

29. The laminate of claim 28, wherein the elastic laminate exhibits a creeping percentage less than about 50%.

30. The laminate of claim 29, wherein the elastic laminate exhibits a creeping percentage less than about 20%.

31. The laminate of claim 15, wherein the fibrous sheet is selected from a group consisting of spunbond sheets, meltblown sheets, and combinations thereof.

32. An absorbent article comprising the laminate of claim 15.

33. A laminate, comprising:
a polymer composite including a polymer material and a microwave sensitizer material blended with the polymer material, the polymer composite having a first elastic state and a second latent state when stretched to a predetermined length; and
a fibrous sheet bonded to the polymer composite.

34. The laminate of claim 33, wherein the fibrous sheet is bonded to the polymer composite in the second latent state and exposed to at least one of microwave energy and thermal energy.

35. The laminate of claim 33, wherein the polymer composite comprises one of a filament, a film, and combinations thereof.

36. The laminate of claim 33, wherein the polymer material is selected from a group consisting of polyether-block amides, ethylene-vinylacetate block or random copolymers, polyethylene-polyethylene oxide block copolymers, polypropylene oxide-polyethylene oxide block copolymers, polyesters, polyurethanes, polyacrylates, polyethers, and combinations thereof.

37. The laminate of claim 33, wherein the sensitizer material is selected from a group consisting of carbon black powder, calcium chloride, aluminum oxide, copper oxide, zinc oxide, barium ferrite, magnesium ferrite, magnesium acetate, and combinations thereof.

38. The laminate of claim 33, wherein the polymer material includes about 1% to about 20% by weight of sensitizer material.

39. The laminate of claim 33, wherein the sensitizer is substantially uniformly blended with the polymer material and the polymer composite includes a rough surface texture.

40. The laminate of claim 33, wherein the fibrous sheet includes a nonwoven sheet selected from a group consisting of spunbond sheets, meltblown sheets, and combinations thereof.

41. The laminate of claim 40, wherein the nonwoven sheet is bonded to the polymer composite by hot melt adhesive.

42. The laminate of claim 41, wherein the laminate exhibits a creeping percentage less than about 50%.

* * * * *